US012008627B2

(12) United States Patent
Kim et al.

(10) Patent No.: US 12,008,627 B2
(45) Date of Patent: Jun. 11, 2024

(54) SYSTEM FOR RECOMMENDING USER-CUSTOMIZED BEVERAGE THROUGH GENETIC TEST, AND METHOD FOR DRIVING SAME

(71) Applicant: CLINOMICS INC., Ulsan (KR)

(72) Inventors: Byung Chul Kim, Suwon-si (KR); Jong Hwa Bhak, Ulsan (KR); Yun Sung Cho, Yongin-si (KR); Su An Cho, Hwaseong-si (KR)

( * ) Notice: Subject to any disclaimer, the term of this patent is extended or adjusted under 35 U.S.C. 154(b) by 185 days.

(21) Appl. No.: 17/621,537

(22) PCT Filed: Aug. 26, 2019

(86) PCT No.: PCT/KR2019/010836
§ 371 (c)(1),
(2) Date: Dec. 21, 2021

(87) PCT Pub. No.: WO2021/033817
PCT Pub. Date: Feb. 25, 2021

(65) Prior Publication Data
US 2022/0358561 A1 Nov. 10, 2022

(30) Foreign Application Priority Data

Aug. 16, 2019 (KR) .................. 10-2019-0100369

(51) Int. Cl.
*G06Q 30/00* (2023.01)
*A61B 5/00* (2006.01)
(Continued)

(52) U.S. Cl.
CPC .......... *G06Q 30/0631* (2013.01); *A61B 5/021* (2013.01); *A61B 5/4869* (2013.01); *A61B 5/7275* (2013.01); *G06Q 30/0621* (2013.01)

(58) Field of Classification Search
CPC ............ G06Q 30/0631; G06Q 30/0621; A61B 5/021; A61B 5/4689; A61B 5/7275
See application file for complete search history.

(56) References Cited

U.S. PATENT DOCUMENTS

| 2006/0081653 A1* | 4/2006 | Boland | ................. G16H 20/60 222/243 |
|---|---|---|---|
| 2010/0112570 A1 | 5/2010 | Aziz et al. | |

(Continued)

FOREIGN PATENT DOCUMENTS

| KR | 10-2010-0084611 | 7/2010 |
|---|---|---|
| KR | 10-2010-0137676 | 12/2010 |

(Continued)

OTHER PUBLICATIONS

Derossi, Antonio, et al. "Manufacturing personalized food for people uniqueness. an overview from traditional to emerging technologies." Critical reviews in food science and nutrition 60.7 (2020): 1141-1159.*

(Continued)

*Primary Examiner* — Kathleen Palavecino
(74) *Attorney, Agent, or Firm* — ANTONIO HA & U.S. PATENT, LLC

(57) ABSTRACT

The present invention may provide a system for recommending a user-customized beverage through a genetic test, and a method for driving same, the system comprising: a genetic information acquisition unit for acquiring user's genetic information from a result of a user's genetic test; and a beverage recommendation unit for recommending at least one user-customized recommendable beverage on the basis of the genetic information acquired from the genetic information acquisition unit, wherein the system for recommending a user-customized beverage through a genetic test can (Continued)

recommend a customized-beverage to a user by reflecting a genotype through the user's genetic test.

6 Claims, 3 Drawing Sheets

(51) Int. Cl.
    *A61B 5/021*     (2006.01)
    *G06Q 30/0601*     (2023.01)

(56) References Cited

U.S. PATENT DOCUMENTS

| | | | |
|---|---|---|---|
| 2010/0312668 A1* | 12/2010 | Notsani | G06Q 30/02 705/26.63 |
| 2018/0144820 A1 | 5/2018 | Grimmer et al. | |
| 2018/0374567 A1 | 12/2018 | Toumazou et al. | |
| 2019/0133454 A1* | 5/2019 | Mou | A61B 5/02141 |

FOREIGN PATENT DOCUMENTS

| | | |
|---|---|---|
| KR | 10-2011-0081861 | 7/2011 |
| KR | 10-2017-0054628 | 5/2017 |
| KR | 10-2018-0020691 | 2/2018 |
| KR | 10-2018-0114612 | 10/2018 |
| KR | 10-1915747 | 11/2018 |
| WO | WO2005111955 A1 | 11/2005 |

OTHER PUBLICATIONS

English Specification of 10-2011-0081861.
English Specification of 10-2018-0114612.
English Specification of 10-2017-0054628.
English Specification of 10-1915747.
English Specification of 10-2010-0137676.
English Specification of 10-2010-0084611.
English Specification of 10-2018-0020691.

* cited by examiner

SYSTEM FOR RECOMMENDING USER-CUSTOMIZED BEVERAGE THROUGH GENETIC TEST, AND METHOD FOR DRIVING SAME

TECHNICAL FIELD

The present invention relates to a user-customized beverage recommendation system and a driving method thereof through a genetic test, and more particularly, to a user-customized beverage recommendation system and a driving method thereof through a genetic test, which further reflects the user's beverage preference.

BACKGROUND ART

Genetic testing is a test for genes contained in chromosomes and may diagnose genetic diseases or some tumors, mutations, and chromosomal abnormalities. Test methods include polymerase chain reaction (PCR) or DNA sequencing, chromosomal microarray (CMA) or chromosome test (karyotyping), fluorescence in situ hybridization, FISH) and the like.

It is possible to check a user's health through genetic testing and provide a medical treatment suitable for the user.

Korean Patent Application Publication No. 2011-0081861 discloses a method and a test method capable of establishing a weight loss program for each testee based on the testee's metabolic genotype of a key metabolic gene.

This method recommends the testee for an appropriate treatment/diet or lifestyle. In the method, the testee's genotype is examined from one or more loci selected from the group consisting of IL-1B, IL-1A, IL-1RN ADRB2, ADRB3 and MCR4 and predicts the testee's predisposition to weight loss, which reacts to a low calorie diet, or a liquid diet, or both, from the presence of one or more alleles in the locui.

In other words, the testee's likelihood of reaction to a given diet and activity level is used to recommend an appropriate treatment/diet or lifestyle, thereby making it possible to determine the testee's metabolic genotype.

The per-person weight loss program provides better effects in terms of weight loss and weight maintenance as compared to traditional weight loss programs that do not consider genetic information.

Meanwhile, coffee consumption has been on the rise in recent years. Due to the variety of flavors and ingredients, it is somewhat difficult to choose a beverage that suits one's preference if he/she does not have professional knowledge about coffee.

DETAILED DESCRIPTION OF THE INVENTION

Technical Problems

The present invention has been conceived in light of the foregoing technical background and aims to provide a user-customized beverage recommendation system and a driving method thereof through a genetic test, which may recommend a customized beverage to the user by reflecting the user's genotype through a genetic test on the user.

There is also provided a user-customized beverage recommendation system and a driving method thereof through a genetic test, which may make the same beverage differently for each user by reflecting the user's health condition and taste preference and facilitates ordering.

Means to Address the Problems

To achieve the above objectives, the present invention includes the following components.

According to an embodiment of the present invention, a user-customized beverage recommendation system through a genetic test comprises a genetic information acquisition unit obtaining user genetic information about a user from a result of a genetic test on the user and a beverage recommendation unit recommending at least one user-customized recommended beverage based on the genetic information obtained by the genetic information acquisition unit.

Meanwhile, a method for driving a user-customized beverage recommendation system through a genetic test comprises obtaining user genetic information from a result of a genetic test on the user, by a genetic information acquisition unit and recommending at least one user-customized recommended beverage based on the obtained genetic information, by a beverage recommendation unit.

Effects of the Invention

According to the present invention, it is possible to provide a user-customized beverage recommendation system and a driving method thereof through a genetic test, which may recommend a customized beverage to the user by reflecting the user's genotype through a genetic test on the user.

It is also possible to provide a user-customized beverage recommendation system and a driving method thereof through a genetic test, which may make the same beverage differently for each user by reflecting the user's health condition and taste preference and facilitates ordering.

BEST MODE TO PRACTICE THE INVENTION

The terms as used herein are provided merely to describe some embodiments thereof, but not to limit the present disclosure. The terms as used herein are provided merely to describe some embodiments thereof, but not to limit the scope of other embodiments of the present disclosure. Unless otherwise defined, all terms including technical and scientific terms used herein have the same meaning as commonly understood by one of ordinary skill in the art to which the embodiments of the present invention pertain and should not be interpreted as overly broad or narrow.

Hereinafter, preferred embodiments of the present invention are described in detail with reference to the accompanying drawings.

Figure 1:
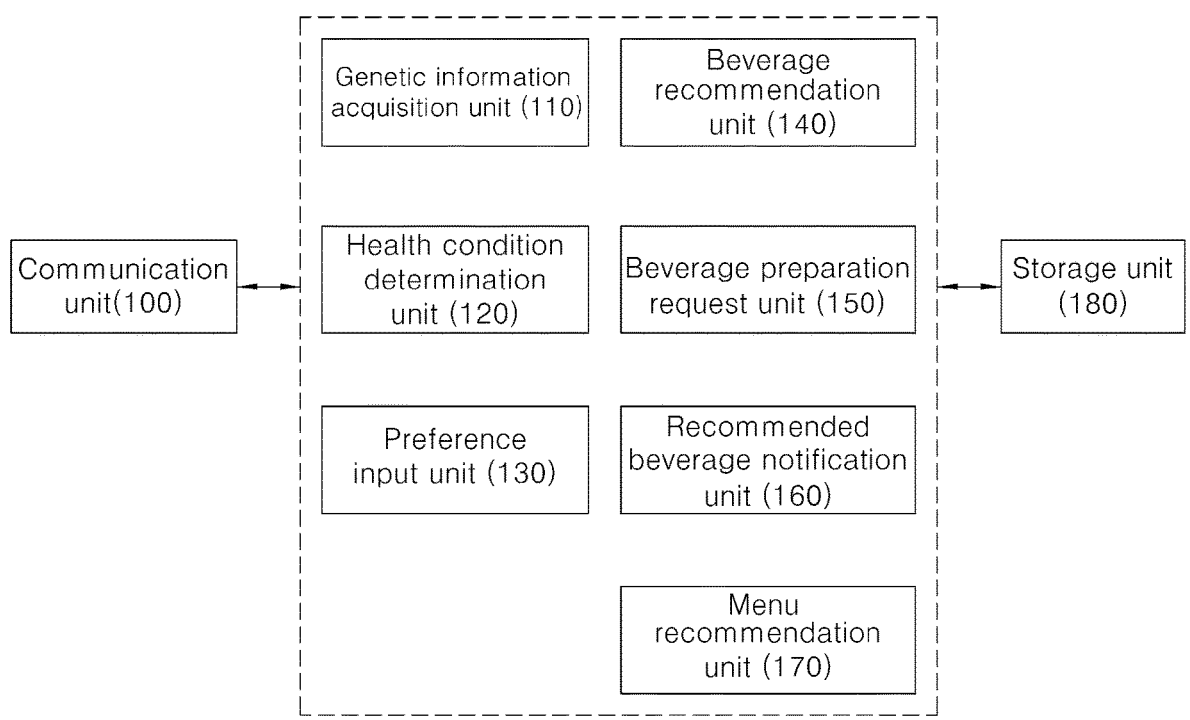
FIG. 1 is a block diagram illustrating a configuration of a user-customized beverage recommendation system according to an embodiment of the present invention.

FIG. 1 is a block diagram illustrating a configuration of a user-customized beverage recommendation system according to an embodiment of the present invention.

In an embodiment, the user-customized beverage recommendation system through a genetic test may be implemented as a service providing server capable of establishing a user-customized beverage recommendation service providing platform.

Further, the service providing server may be provided in a genome cafe that integrates and provides an offline genetic test service for providing a genetic test and a cafe service for selling beverages. However, the present invention is not limited thereto, and a service providing server for integrated management of cafe terminals provided in a plurality of genome cafes.

The user-customized beverage recommendation system through a genetic test stores information regarding genetic test results and the quantity, frequency, and type coffee consumption for members who have signed up for membership using the genome cafe, as bigdata.

The genome cafe not only sells beverages but may also serve as an offline genetic test center for items that are permitted for genetic testing in a direct-to-consumer (DTC) type.

Further, according to an embodiment, the user-customized beverage recommendation system through a genetic test may display the correlation between coffee depending on the amount of caffeine and the caffeine genotype through a mobile application executed on the user terminal and provide information about, e.g., the type of beverage most suitable for the user, type of coffee, frequency of consumption, and the amount of consumption.

Referring to FIG. 1, according to an embodiment, the user-customized beverage recommendation system includes a communication unit 100, a genetic information acquisition unit 110, a health condition determination unit 120, a preference input unit 130, a beverage recommendation unit 140, a beverage preparation request unit 150, a recommended beverage notification unit 160, and a storage unit 180.

The communication unit 100 communicates with the user terminal where a user-customized beverage recommendation dedicated application is executed. Further, the communication unit 100 may be connected, through a network, with a cafe terminal, which is provided in the cafe to receiving orders, and a body composition meter or blood pressure meter.

The network may include at least one of a personal area network (PAN), a local area network (LAN), a campus area network (CAN), a metropolitan area network (MAN), a wide area network (WAN), a broadband network (BBN), or the Internet.

The network may include, but is not limited to, at least one network topology including a bus network, a star network, a ring network, a mesh network, a star-bus network, or a tree or hierarchical network.

Further, the communication unit 100 is interpreted as including various schemes of wireless communication, e.g., near field communication (NFC), Bluetooth, RFID, Zigbee, or other short-range wireless communication modules.

The genetic information acquisition unit 110 obtains genetic information about the user from the results of the genetic test on the user.

In an embodiment, the genetic information acquisition unit 110 obtains the genetic test results from a genetic test kit provided in the genome cafe. For example, the genetic test kit performs the genetic test using the user's saliva or oral epithelium.

The genetic information obtainable from the genetic information acquisition unit 110 may include at least one of caffeine decomposition ability, sweet taste preference, sweet taste sensitivity, sour taste preference; bitter taste sensitivity, lactose decomposition ability, body mass index, hair thickness, hair loss, blood pressure, skin aging state, skin elasticity state, vitamin C concentration, cholesterol, triglyceride, and blood sugar. However, without being limited thereto, the genetic information obtainable through the genetic test may further include other various items.

In one aspect, the genetic information acquisition unit 110 transmits the obtained user genetic information to the user terminal through the communication unit 100. Then, the user-customized beverage recommendation dedicated application of the user terminal may display the user genetic information received from the genetic information acquisition unit 110 on the screen. In other words; the user may immediately and comfortably identify his or her genetic test results using the user terminal.

The health condition determination unit 120 receives the user's biometric signal from the body composition meter or the blood pressure meter to determine the user's health condition.

According to the present aspect, the genome cafe is equipped with a medical device by which the user may check his physical condition, that is, the health condition, even without visiting the hospital. The health state determination unit 120 may receive the biometric signal measured from the medical device, along with the user's genetic test result, determining the user's health condition.

For example, the health condition determination unit 120 may obtain the results of body composition measurement from the body composition meter and determine the user's body mass index, visceral fat, or the like from the obtained results of body composition measurement. Further, the health condition determination unit 120 may receive the user's blood pressure information from the blood pressure meter to determine the user's blood pressure state.

The preference input unit 130 receives information about the user's beverage preference. In an embodiment, the preference input unit 130 receives user beverage preference information from the user terminal through the communication unit 100.

In this case, the user-customized beverage recommendation dedicated application executed on the user terminal may provide a question list for receiving entry for the user's beverage or taste preference and may determine the user's beverage or taste preference based on entered, selected items. In other words, the user-customized beverage recommendation dedicated application may provide various types of user interfaces for identifying the users beverage preference.

The preference input unit 130 may receive preferences and tastes for each taste through a user interface that provides a step-by-step selection of preferences for each of sweet, sour, salty, bitter, and umami flavors.

The preference input unit 130 provides some or all items in the form of a questionnaire through the user-customized beverage recommendation dedicated application of the user terminal to identify the user's beverage or taste preference.

The beverage recommendation unit 140 recommends at least one user-customized recommended beverage based on the genetic information obtained from the genetic information acquisition unit 110.

The beverage recommendation unit 140 may set nutrients and intake amount required for the user, based on personal genetic information.

The beverage recommendation unit 140 may extract physical or environmental factors directly associated with genetic mutation from the personal genetic information and may obtain the user's unique eating habits information from the extracted physical or environmental factors.

According to an aspect, the beverage recommendation unit 140 may further reflect the user's health condition determined by the health condition determination unit 120 or the user's beverage preference input to the preference input unit 130 in recommending the user-customized recommended beverage.

The beverage recommendation unit 140 may recommend a beverage good for the user's health condition based on the body mass index, hair thickness, blood pressure, skin condition, cholesterol information, triglyceride information, and blood sugar information, which may be identified by genetic factors according to the genetic test result.

The beverage recommendation unit 140 generates specification information about the recommended beverage by determining the type of the recommended beverage, whether to add additives to the beverage, and adjusting the amount of additives according to the body mass index and the risk of hair loss which are examples of genetic information.

Table 1 below may be referenced in determining the recommended beverage by reflecting the genetic test results. However, this is merely an example and is not limited thereto.

TABLE 1

| Genetic test results (related phenotypes are bundled) | Recommended beverages |
|---|---|
| high body mass index | green tea, black tea, chamomile tea, cinnamon tea, mate tea, grape juice |
| thin hair, risk of hair loss | green tea, black tea, black bean/black sesame drink, pomegranate tea, donggul tea, goji tea |
| high blood pressure | green tea, cinnamon tea, black tea, citron tea, yulmu tea, mulberry leaf tea, plum tea, chrysanthemum tea |
| high skin aging, low skin elasticity, low vitamin C concentration | green tea, orange, banana, tomato, lemon tea, jasmine, barley tea, grapefruit tea, goji berry tea |
| high total cholesterol/ high triglycerides | strawberry, apple, green tea, barley tea, tomato, kiwi, carrot, low-fat yogurt |
| high blood sugar | green tea, black tea, tomato, apple, blueberry, grapefruit, kiwi, strawberry, banana |

Based on Table 1, the beverage recommendation unit 140 recommends green tea as a first-priority recommended beverage, e.g., for users with high body mass index and high risk of hair loss. Further, the beverage recommendation unit 140 recommends black tea, chamomile, cinnamon tea, mate tea, grape juice, black bean/black sesame drink, pomegranate tea, donggul tea, and goji tea, as second-priority recommended beverages, for users with high body mass index or risk of hair loss. Further, the beverage recommendation unit 140 recommends green tea and cinnamon tea, as first-priority recommended beverages, for users with both high body mass index and high blood pressure. In other words, it is possible to provide recommended beverages in the order of the first priority, second priority, third priority, . . . , depending on the user's health condition.

If a signal of selecting a user customized recommended beverage from among at least one recommended beverage recommended by the beverage recommendation unit 140 is input from the user terminal where the user customized beverage recommendation dedicated application is executed, the beverage preparation request unit 150 transmits the specification information about the user customized recommended beverage to the cafe terminal and requests to prepare the beverage.

In other words, the user may select one or more from at least one or more user-customized beverages reflecting his/her genetic information, recommended in the user-customized beverage recommendation dedicated application. The user may order the selected beverage simultaneously with selection. In other words, the user may receive recommendations for customized beverages using the user-customized beverage recommendation dedicated application according to an embodiment, select one of the recommended beverages, and order and pay for the selected beverage.

The beverage preparation request unit 150 may include, as specifications of a user-customized recommended beverage, the type of coffee beans, the degree of grinding of coffee beans, a method for making coffee, whether to add syrup and the amount added, whether to add fresh cream or m ilk and the amount added, and, if the beverage is a fruit juice, the type and content of fruits or vegetables added.

Accordingly, it is possible to reduce the hassle and waiting time of having to order at the counter.

In another embodiment, when the user brings the user terminal close to the cafe terminal, the user terminal may transmit the specification information about the selected user-customized recommended beverage to the cafe terminal to request to prepare the beverage.

In this case, the user terminal transmits the specification information about the user-customized recommended beverage to the cafe terminal in a short-range wireless communication scheme, e.g., RFID.

According to an embodiment, the beverage recommendation unit 140 may generate user-customized recommended beverage information and recommended beverage specification information about the beverage and transmit it to the cafe terminal or the user terminal.

The beverage recommendation unit 140 reflects at least one of caffeine decomposition ability, sensitivity to bitter taste, sour taste preference, sweet taste preference, and lactose decomposition ability, and recommends a coffee making method.

As an example, the gene phenotypes according to the genetic test results related to coffee tastes are shown in Table 2 below. However, this is merely an example and is not limited thereto.

TABLE 2

| Phenotypes | Related characteristics | RSID | gene | risk factor |
|---|---|---|---|---|
| sweetness | high preference | rs838133 | FGF21 | T |
|  | high sensitivity | rs307355 | TAS1R3 | C |
| sourness | high preference | rs236514 | KCNJ2 | A |
| saltiness | high sensitivity | rs3785368 | SCNN1B | C |
| bitterness (caffeine) | high sensitivity | rs2597979 | PRH1 | G |
|  | high sensitivity | rs2708377 | TAS2R46 | G |
| bitterness (phenylthiol-carbamide) | high sensitivity | rs173598 | TAS2R38 | C |
| umami | high sensitivity | rs307377 | TAS1R3 | T |
| lactose decomposition | high decomposition ability | rs4988235 | MCM6 | T |

In general, it is reported that arabica coffee has about half the caffeine content of robusta coffee. Further, among various making methods, it is reported that brewing (for raw coffee beans) reduces caffeine content than dripping and espresso making. Therefore, if the user's ability to decompose caffeine is low, the user may be recommended arabica beans rather than robusta beans and brewed coffee rather than dripped coffee and espresso.

Further, the bitterness/sourness of coffee may be determined depending on the degree of roasting, degree of grinding, extraction amount, extraction temperature, number of times of extraction, and the like, and the sweetness and lactose may be adjusted by adding sugar/syrup and milk/fresh cream. Thus, the method of making coffee (beverage) is adjusted according to the test results and the preference shown in the questionnaire preference and is then recommended.

The type of coffee, making method and the amount of syrup or milk/fresh cream added may be changed and recommended.

For example, if the user has a relatively high preference to sweetness, the amount of syrup added may be adjusted to 3 and, if the user has a relatively low preference to sweetness, the amount of syrup added may be adjusted to 1. In this case, a reference for the amount of syrup added depending on the preference to sweetness may be arbitrarily set and changed.

The recommended beverage notification unit 160 provides information about the user-customized recommended beverage recommended by the beverage recommendation unit 140, to the user-customized beverage recommendation dedicated application of the user terminal through the communication unit 100, every period set by the user.

In other words, if the user sets a notification through the user-customized beverage recommendation dedicated application, the user may receive a recommendation for coffee or beverage optimized for the user at each set time daily. In this case, the user may pre-order the recommended coffee or beverage through the user-customized beverage recommendation dedicated application and get the pre-ordered beverage or coffee at the cafe at the reserved time.

Further, if the user brings the user terminal close to the cafe terminal, the cafe terminal may output the information about the user-customized recommended beverage based on user information recognized from the user terminal. Further, the cafe terminal may directly obtain the specification information about the user-customized recommended beverage from the user-customized beverage recommendation system according to an embodiment.

Further, according to an embodiment, the user-customized beverage recommendation system may further recommend a customized diet method, health functional food, customized lunch box menu, or cosmetics based on the genetic test.

In this case, in recommending health functional foods or customized lunch boxes, the user-customized beverage recommendation system may recommend health functional foods including nutrients capable of enhancing health functions when eaten or necessary nutrients depending on the results of genetic test on the user or the results of determining the user's health condition.

According to an additional aspect of the present invention, the user-customized beverage recommendation system according to an embodiment further includes a menu recommendation unit 170 that determines the lunch box menu selling in a specific lunch box company and selects and provides a lunch box, which contains a large amount of nutrients genetically effective for the user, from the lunch box menu.

The menu recommendation unit 170 may recommend a menu item rich in effective nutrients for the user or may recommend a recipe for the menu item. In this case, the recipe may be extracted from specification information uploaded on a webpage by web scrolling and provided. For example, among recipes uploaded on social media, a recipe may be extracted and provided which reflects the user's preference and contains preferred ingredients and the content of sodium.

In this case, the preferred ingredients and the preferred recipe may be information obtained through a survey in the preference input unit 130.

The menu recommendation unit 170 may obtain the user's current GPS signal-based location information from the user terminal and recommend lunch box sellers, located within a radius of several kilometers of the user's current location or restaurant menu.

According to an auxiliary aspect of the present invention, the user-customized beverage recommendation system according to an embodiment further provides a friend recommendation function of matching others with similar personalities, propensities, or affectional tendencies. As users with similar genetic information or favoring the same beverage or taste share the recipe or menu, efficient online or offline communication is possible between users with similar preferences to food.

In other words, the user may view the reviews of others who have similar food preferences and may thus obtain review information with high consensus on other beverages or foods in addition to the recommended beverage.

The storage unit 180 stores, as bigdata, genetic information about users with membership (i.e., members) and information about the amount, frequency, and type of coffee consumption. In other words, the storage unit stores, as bigdata, the user's genetic information obtained by the genetic information acquisition unit 110, the user's health condition identified by the health condition determination unit 120, and the user's beverage/food taste preference information input by the preference input unit 130.

Figure 2:
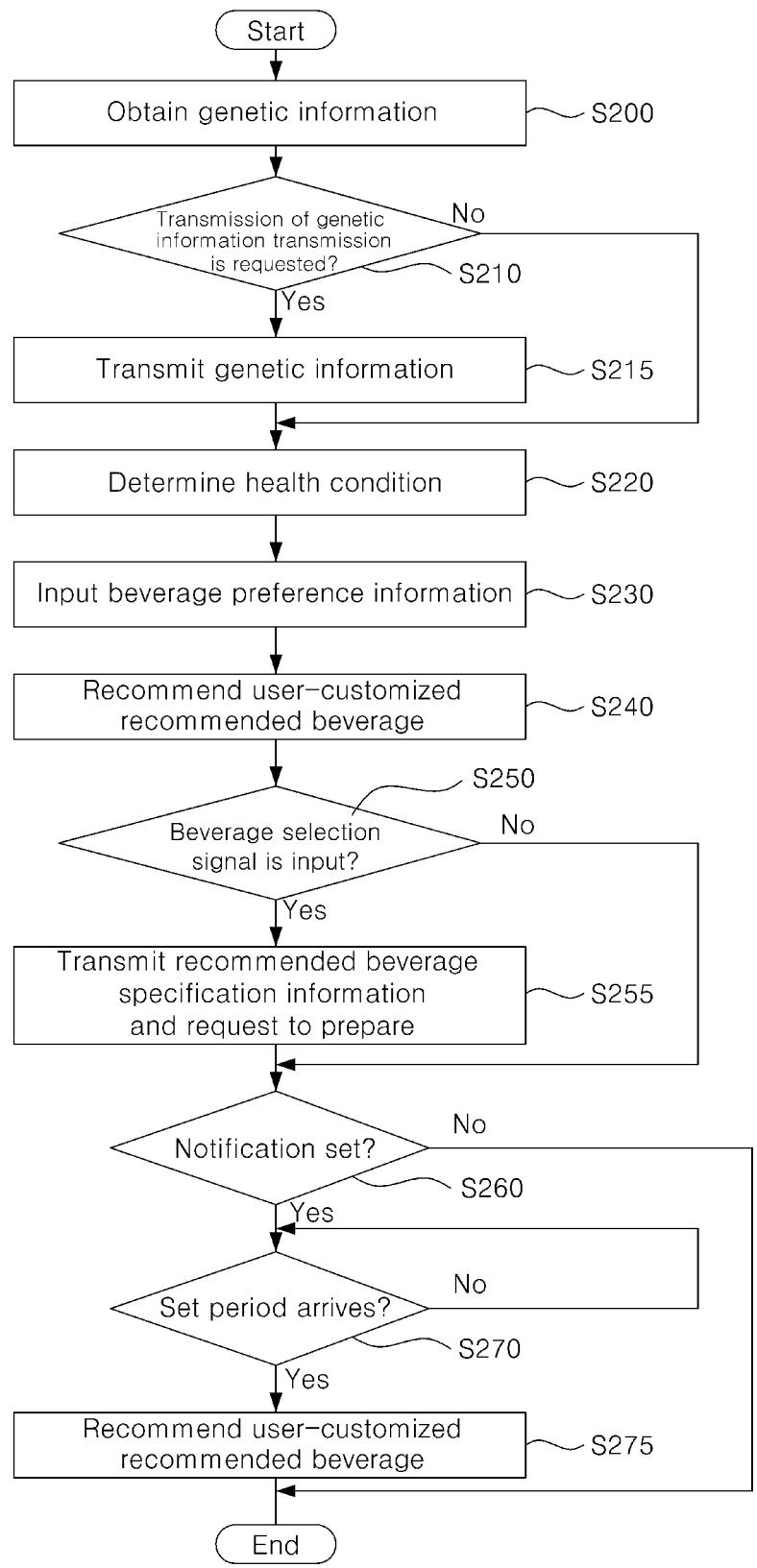
FIG. 2 is a flowchart illustrating a method for driving a user-customized beverage recommendation system through a genetic test according to an embodiment of the present invention.

FIG. 2 is a flowchart illustrating a method for driving a user-customized beverage recommendation system through a genetic test according to an embodiment of the present invention.

First, in a method for driving a user-customized beverage recommendation system through a genetic test, the genetic information acquisition unit obtains the user's genetic information from the user's genetic test result (S200).

According to an embodiment, obtaining genetic information may be obtaining the genetic test result from a genetic test kit equipped in the genome cafe. For example, the genetic test kit performs the genetic test using the user's saliva or oral epithelium.

The genetic information obtainable may include at least one of caffeine decomposition ability, sweet taste preference, sweet taste sensitivity, sour taste preference, bitter taste sensitivity, lactose decomposition ability, body mass index, hair thickness, hair loss, blood pressure, skin aging state, skin elasticity state, vitamin C concentration, cholesterol, triglyceride, and blood sugar. However, without being limited thereto, the genetic information obtainable through the genetic test may further include other various items.

Thereafter, when receiving a request to transmit genetic information from the user terminal (S210), the genetic information acquisition unit transmits the obtained user genetic information to the user terminal (S215).

Then, the user-customized beverage recommendation dedicated application of the user terminal may display the user genetic information on the screen. In other words, the user may immediately and comfortably identify his or her genetic test results using the user terminal.

Thereafter, according to an aspect of the present invention, the health condition determination unit receives the user's biometric signal from the body composition meter or blood pressure meter to grasp the user health condition (S220).

For example, grasping the health condition may obtain the results of body composition measurement from the body composition meter and determine the user's body mass index, visceral fat, or the like from the obtained results of body composition measurement. Further, the health condition determination unit 120 may receive the user's blood pressure information from the blood pressure meter to determine the user's blood pressure state.

Further, the preference input unit receives information about the user's beverage preference (S230). In an embodiment, the preference input unit receives the user's beverage preference information from the user terminal.

Receiving the preference information may receive preferences and tastes for each taste through a user interface that provides a step-by-step selection of preferences for each of sweet, sour, salty, bitter, and umami flavors.

In other words, some or all items are provided in the form of a questionnaire through the user-customized beverage recommendation dedicated application of the user terminal to identify the user's beverage or taste preference.

The beverage recommendation unit recommends at least one user-customized recommended beverage based on the obtained genetic information (S240).

According to an aspect, the beverage recommendation unit further reflects the user's health condition, which is obtained, or the user's beverage/taste preference, which is input to the preference input unit, and recommends the user-customized recommended beverage.

In this case, the beverage recommendation unit may recommend a beverage good for the user's health condition based on the body mass index, hair thickness, blood pressure, skin condition, cholesterol information, triglyceride information, and blood sugar information, which may be identified by genetic factors according to the genetic test result.

The beverage recommendation unit 140 generates specification information about the recommended beverage by determining the type of the recommended beverage, whether to add additives to the beverage, and adjusting the amount of additives according to the body mass index and the risk of hair loss which are examples of genetic information.

Thereafter, if a signal for selecting a user-customized recommended beverage is input through the user terminal where the user-customized beverage recommendation dedicated application is executed (S250), the beverage preparation request unit transmits the specification information about the selected user-customized recommended beverage to the cafe terminal, thereby requesting to prepare the beverage (S255).

In this case, the specifications of the user-customized recommended beverage include the type of coffee beans, the degree of blindness of coffee beans, the coffee manufacturing method, whether syrup is added and the amount added, whether fresh cream or milk is added and the amount added, the type of fruit or vegetables added in the case of fruit juice, and Content information may be included.

Accordingly, it is possible to reduce the hassle and waiting time of having to order at the counter.

In another embodiment, if the user brings the user terminal close to the cafe terminal, the user terminal may transmit the specification information about the selected user-customized recommended beverage to the cafe terminal to request to prepare the beverage. In this case, the user terminal transmits the specification information about the user-customized recommended beverage to the cafe terminal in a short-range wireless communication scheme, e.g., RFID.

When the user sets a notification (S260), the recommended beverage notification unit provides the information about the user-customized recommended beverage recommended in the recommending step to the user-customized beverage recommendation dedicated application of the user terminal every period (S270) set by the user (S275).

In other words, if the user sets a notification through the user-customized beverage recommendation dedicated application, the user may receive a recommendation for coffee or beverage optimized for the user at each set time daily. In this case, the user may pre-order the recommended coffee or beverage through the user-customized beverage recommendation dedicated application and get the pre-ordered beverage or coffee at the cafe at the reserved time.

Figure 3:
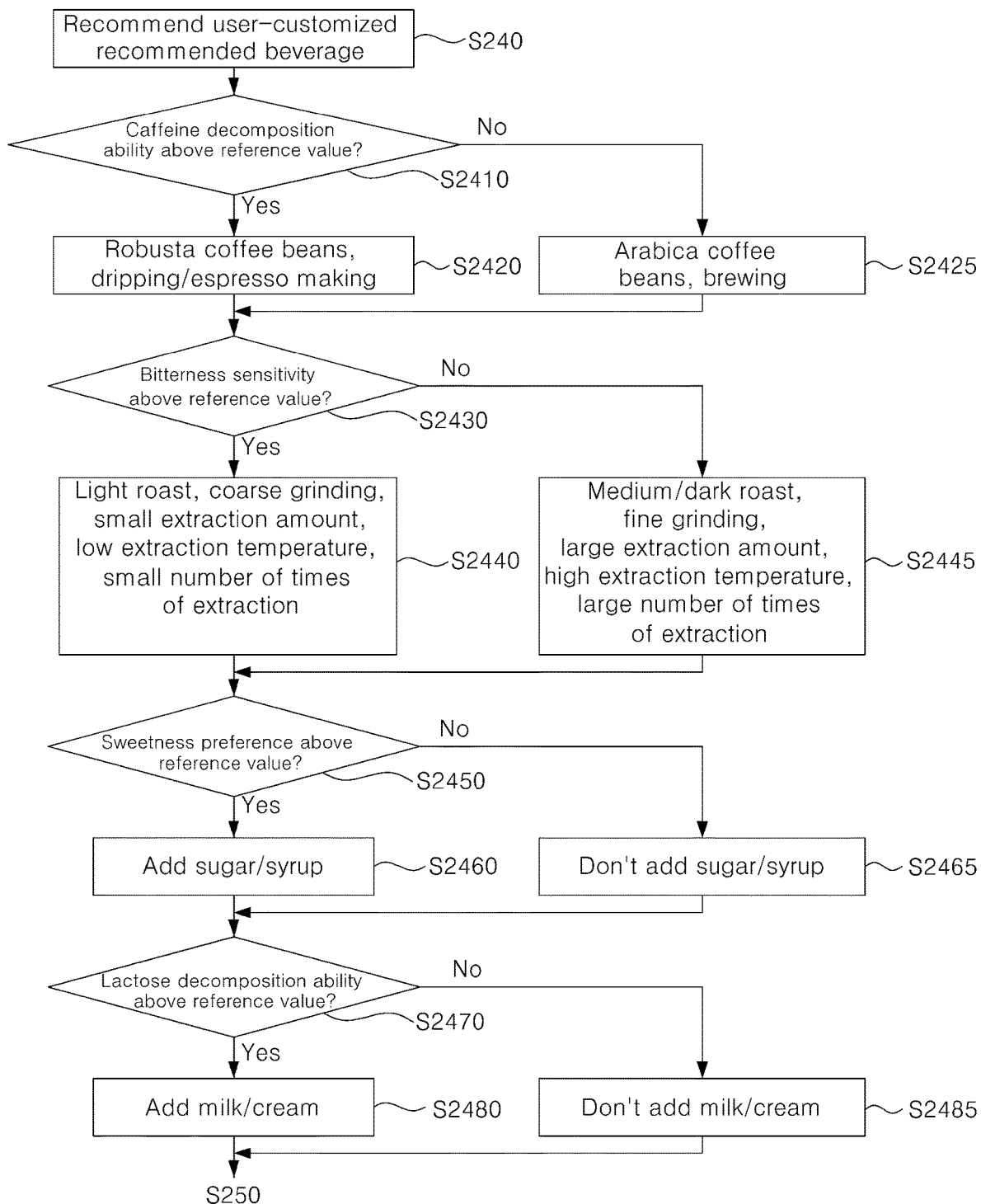
FIG. 3 is a flowchart illustrating, in greater detail, a beverage recommendation process according to an embodiment of the present invention.

FIG. 3 is a flowchart illustrating, in greater detail, a beverage recommendation process according to an embodiment of the present invention.

As illustrated in FIG. 3, in recommending the user-customized beverage, first, the beverage recommendation unit determines whether the user's caffeine decomposition ability is larger than or equal to a reference value (S2410). In this case, the reference value of the caffeine decomposition ability may be arbitrarily set by a service provider or the user. The caffeine decomposition ability may be expressed as a numerical value or may be determined by a relative percentage of users who use the service.

It is reported that *Arabica* coffee has about half the caffeine content of *Robusta* coffee. Further, among various making methods, it is reported that brewing (for raw coffee beans) reduces caffeine content than dripping and espresso making.

Therefore, for users with relatively good caffeine decomposition ability, robusta coffee beans are recommended. As a making method, dripping or espresso making is recommended (S2420).

In contrast, for users with a relatively low caffeine decomposition ability, arabica coffee beans and brewing, as the coffee making method, are recommended (S2425).

Then, it is determined whether the user's sensitivity to bitter taste is larger than or equal to a reference value (S2430). Bitter taste sensitivity may be identified from user preference information. If the sensitivity to bitter taste is equal to or higher than the reference value or if the bitter taste of coffee is not preferred, specification information about the user-customized recommended beverage, which includes light roasting, coarse coffee grinding, small extraction amount, low extraction temperature, and small number of times of extraction, is generated (S2440).

In contrast, if the sensitivity to bitter taste is lower or the bitter taste of coffee is preferred, specification information about the user-customized recommended beverage, which includes medium/dark roasting, a large extraction amount, a high extraction temperature, and a large number of times of extraction, is generated (S2445).

In this case, the degree of roasting, the large or small extraction amount, high or low extraction temperature, and the large or small number of times of extraction are relative representations of the physical amounts. In the present invention, the degree of roasting, the amount of extraction, the extraction temperature, the number of times of extraction, etc., are not limited to absolute values. In other words, the degree of roasting, the amount of extraction, the extraction temperature, the number of times of extraction, etc. may be arbitrarily set or changed by a service provider or the user who tastes the beverage.

Then, it is determined whether the user's sensitivity to sweet taste is larger than or equal to a reference value (S2450). Sweet taste sensitivity may be identified from user preference information. The specification information about the user-customized recommended beverage is generated so that for users having a sweet taste preference above the reference value, sugar/syrup is added (S2460) and, for users having a low sweet taste preference, sugar or syrup is not added (S2465).

Further, the sweet taste preference may be divided into at least two or more steps to set different amounts of sugar or syrup to be added. For example, the amount of sugar or syrup added may be set to differ depending on the degree of the user's preference to sweet taste. For users with a very high preference to sweetness, the amount of syrup added may be set to three pumps and, for users with a little high preference to sweetness, the amount of syrup added may be set to two pumps. As such, other various settings may be made. Accordingly, it is possible to more precisely recommend a customized beverage that fits the user's taste.

Further, it is determined whether the user's lactose decomposition ability is larger than or equal to a reference value (S2470). In this case, the user's lactose decomposition ability may be determined reflecting the user's genetic information and age.

Further, the specification information about the user-customized recommended beverage is generated so that if the lactose decomposition ability is equal to or more than the reference value, milk and cream are added to coffee or beverage (S2480), and if the lactose decomposition ability is lower than the reference value, milk or cream is not added (S2485).

In this case, whether to add milk or cream and the user's lactose decomposition ability may be divided into steps and grasped to change the type of milk or cream or adjust stepwise the amount added.

The above-described method may be implemented as an application or in the form of program instructions executable through various computer components, which may then be recorded in a computer-readable recording medium. The computer-readable medium may include programming commands, data files, or data structures, alone or in combinations thereof.

The programming commands recorded in the computer-readable medium may be specially designed and configured for the present invention or may be known and available to one of ordinary skill in the computer software industry.

Examples of the computer readable recording medium may include, but is not limited to, magnetic media, such as hard disks, floppy disks or magnetic tapes, optical media, such as CD-ROMs or DVDs, magneto-optical media, such as floptical disks, memories, such as ROMs, RAMs, or flash memories, or other hardware devices specially configured to retain and execute programming commands.

Examples of the programming commands may include, but are not limited to, high-level language codes executable by a computer using, e.g., an interpreter, as well as machine language codes as created by a compiler. The above-described hardware devices may be configured to operate as one or more software modules to perform processing according to the present invention and vice versa.

While the present invention has been shown and described with reference to exemplary embodiments thereof, it will be apparent to those of ordinary skill in the art that various changes in form and detail may be made thereto without departing from the spirit and scope of the present invention as defined by the following claims.

The invention claimed is:

1. A user-customized beverage recommendation system through a genetic test, comprising:
    a communication unit performing communication with a user terminal where a user-customized beverage recommendation dedicated application is executed;
    a genetic information acquisition unit obtaining user genetic information about a user from a genetic test result provided by using a genetic test kit which is performed using the user's saliva or oral epithelium;
    a health condition determination unit determining a user health condition by receiving a user biometric signal from a body composition meter or a blood pressure meter;
    a preference input unit receiving information about a user beverage preference; and
    a beverage recommendation unit recommending at least one user-customized recommended beverage based on the genetic information obtained by the genetic information acquisition unit, wherein the beverage recommendation unit further reflect the user's health condition determined by the health condition determination unit and the user's beverage preference input to the preference input unit in recommending the user-customized recommended beverage,
    wherein the genetic information acquisition unit transmits the obtained user genetic information to the user terminal through the communication unit, and
    wherein the user-customized beverage recommendation dedicated application of the user terminal displays, on a screen, the user genetic information transmitted from the genetic information acquisition unit.

2. The user-customized beverage recommendation system of claim 1, further comprising a beverage preparation request unit requesting to prepare a beverage by transmitting, to a cafe terminal, specification information about the selected user-customized recommended beverage if a signal for selecting the user-customized recommended beverage recommended by the beverage recommendation unit is input from the user terminal where the user-customized beverage recommendation dedicated application is executed.

3. The user-customized beverage recommendation system of claim 1, further comprising a recommended beverage notification unit providing information about the user-customized recommended beverage recommended by the beverage recommendation unit to the user-customized beverage recommendation dedicated application of the user terminal through the communication unit, every period set by the user.

4. A method for driving a user-customized beverage recommendation system through a genetic test, the method comprising:
    obtaining user genetic information from a genetic test result provided by using a genetic test kit which is performed using the user's saliva or oral epithelium, by a genetic information acquisition unit;
    transmitting the obtained user genetic information, through a communication unit performing communication with a user terminal where a user-customized beverage recommendation dedicated application is executed to the user terminal;

determining a user health condition by receiving a user biometric signal from a body composition meter or a blood pressure meter, by a health condition determination unit;

receiving information about a user beverage preference by a preference input unit; and recommending at least one user-customized recommended beverage based on the obtained genetic information, by a beverage recommendation unit, wherein recommending the user-customized recommended beverage further reflects the determined user health condition and the user beverage preference to recommend the user-customized recommended beverage, wherein the genetic information acquisition unit transmits the obtained user genetic information to the user terminal through the communication unit, and wherein the user-customized beverage recommendation dedicated application of the user terminal provides the user genetic information transmitted from the genetic information acquisition unit.

5. The method of claim 4, further comprising requesting, by a beverage preparation request unit, to prepare a beverage by transmitting, to a cafe terminal, specification information about the selected user-customized recommended beverage if a signal for selecting the recommended user-customized recommended beverage is input from the user terminal where the user-customized beverage recommendation dedicated application is executed.

6. The method of claim 4, further comprising providing, by a recommended beverage notification unit, information about the user-customized recommended beverage recommended by the recommending to the user-customized beverage recommendation dedicated application of the user terminal, every period set by the user.

* * * * *